United States Patent
Beraud et al.

(10) Patent No.: US 7,758,615 B2
(45) Date of Patent: Jul. 20, 2010

(54) PARIETAL HOOK

(75) Inventors: Jean-Marc Beraud, St. Etienne (FR); Emmanuel Delorme, Danerey (FR)

(73) Assignee: Colopast A/S, Humlebaek (DK)

( * ) Notice: Subject to any disclaimer, the term of this patent is extended or adjusted under 35 U.S.C. 154(b) by 536 days.

(21) Appl. No.: 11/150,224

(22) Filed: Jun. 13, 2005

(65) Prior Publication Data

US 2005/0288692 A1 Dec. 29, 2005

Related U.S. Application Data

(60) Provisional application No. 60/629,337, filed on Nov. 22, 2004.

(30) Foreign Application Priority Data

Jun. 15, 2004 (FR) ................... 04 06466

(51) Int. Cl.
A61B 17/08 (2006.01)
A61B 17/04 (2006.01)

(52) U.S. Cl. ...................... 606/232; 606/151

(58) Field of Classification Search ................ 606/151, 606/232, 72, 73; 114/218; 43/42.08, 42.1, 43/42.36, 42.37, 42.4, 57.1; D8/367–369; 248/301–308, 215, 339; 24/130, 134 L, 115 M, 24/165, 8, 65, 185, 189, 192, 195, 199, 265, 24/16 R, 127, 129 R, 131; 600/30, 37
See application file for complete search history.

(56) References Cited

U.S. PATENT DOCUMENTS

| 3,839,812 | A | * | 10/1974 | Louthan | .............. | 43/43.6 |
| 4,340,998 | A | * | 7/1982 | Liberge | .............. | 24/130 |
| 5,368,595 | A | | 11/1994 | Lewis | | |
| 5,417,691 | A | * | 5/1995 | Hayhurst | .............. | 606/72 |
| 5,507,796 | A | | 4/1996 | Hasson | | |

(Continued)

FOREIGN PATENT DOCUMENTS

GB 378288 A 8/1932

(Continued)

OTHER PUBLICATIONS

Hardiman, et al. Cystocele repair using polypropylene mesh. Br. J. Obstet. Gynaecol. 107: 825-26 (2000).

(Continued)

*Primary Examiner*—(Jackie) Tan-Uyen T Ho
*Assistant Examiner*—Dianne Dornbusch
(74) *Attorney, Agent, or Firm*—Coloplast Corp., Coloplast A/S; Daniel G. Chapik; Nicholas R. Baumann

(57) ABSTRACT

A surgical device for anchorage of a prosthetic implant with at least one arm or flexible suspension link in muscle or ligament tissues comprises an elongated body, an anchor head located at one end of the body and provided with means of anchorage in the tissues, and at least one orifice, formed in the elongated body to attach to the at least one arm or flexible suspension link, that is associated with a non-return means adapted to enable adjustment of a useful length of the at least one arm or flexible suspension link and to prevent the at least one arm or flexible suspension link from sliding in a direction opposite its direction of insertion.

3 Claims, 2 Drawing Sheets

U.S. PATENT DOCUMENTS

| | | | |
|---|---|---|---|
| 5,522,120 A * | 6/1996 | Brinning | 24/130 |
| 5,596,791 A * | 1/1997 | Parsons | 24/130 |
| 5,669,935 A * | 9/1997 | Rosenman et al. | 606/232 |
| 5,964,782 A * | 10/1999 | Lafontaine et al. | 606/213 |
| 6,221,005 B1 | 4/2001 | Bruckner et al. | |
| 6,273,852 B1 | 8/2001 | Lehe et al. | |
| 6,306,079 B1 | 10/2001 | Trabucco | |
| 6,382,214 B1 | 5/2002 | Raz et al. | |
| 6,387,041 B1 | 5/2002 | Harari et al. | |
| 6,401,309 B1 * | 6/2002 | Yang | 24/130 |
| 6,475,139 B1 | 11/2002 | Miller | |
| 6,494,887 B1 | 12/2002 | Kaladelfos | |
| 6,575,897 B1 | 6/2003 | Ory et al. | |
| 6,786,861 B1 | 9/2004 | Pretorius | |
| 6,908,425 B2 | 6/2005 | Luscombe | |
| 6,932,759 B2 | 8/2005 | Kammerer et al. | |
| 7,083,637 B1 | 8/2006 | Tannhauser | |
| 7,121,997 B2 | 10/2006 | Kammerer et al. | |
| 7,131,943 B2 | 11/2006 | Kammerer | |
| 7,131,944 B2 | 11/2006 | Jacquetin | |
| 7,226,407 B2 | 6/2007 | Kammerer et al. | |
| 2001/0008971 A1 * | 7/2001 | Schwartz et al. | 606/232 |
| 2001/0039423 A1 | 11/2001 | Skiba et al. | |
| 2001/0049467 A1 | 12/2001 | Lehe et al. | |
| 2002/0007222 A1 | 1/2002 | Desai | |
| 2002/0068948 A1 | 6/2002 | Stormby et al. | |
| 2002/0077526 A1 | 6/2002 | Kammerer et al. | |
| 2002/0082619 A1 | 6/2002 | Cabak et al. | |
| 2002/0083949 A1 | 7/2002 | James | |
| 2002/0091298 A1 | 7/2002 | Landgrebe | |
| 2002/0103542 A1 | 8/2002 | Bilbo | |
| 2002/0119177 A1 | 8/2002 | Bowman et al. | |
| 2002/0183588 A1 | 12/2002 | Fierro | |
| 2002/0188169 A1 | 12/2002 | Kammerer et al. | |
| 2003/0023138 A1 | 1/2003 | Luscombe | |
| 2003/0078468 A1 | 4/2003 | Skiba et al. | |
| 2003/0088272 A1 * | 5/2003 | Smith | 606/232 |
| 2003/0100954 A1 | 5/2003 | Schuldt-Hempe et al. | |
| 2003/0120309 A1 * | 6/2003 | Colleran et al. | 606/232 |
| 2003/0149440 A1 | 8/2003 | Kammerer et al. | |
| 2003/0176762 A1 | 9/2003 | Kammerer | |
| 2003/0220538 A1 | 11/2003 | Jacquetin | |
| 2004/0097974 A1 | 5/2004 | DeLaval | |
| 2004/0147958 A1 * | 7/2004 | Lam et al. | 606/232 |
| 2004/0231678 A1 | 11/2004 | Fierro | |
| 2004/0243166 A1 | 12/2004 | Odermatt et al. | |
| 2004/0249240 A1 | 12/2004 | Goldmann et al. | |
| 2004/0267088 A1 | 12/2004 | Kammerer | |
| 2005/0080317 A1 | 4/2005 | Merade | |
| 2005/0107805 A1 | 5/2005 | Bouffier et al. | |
| 2005/0240076 A1 | 10/2005 | Neisz et al. | |
| 2006/0058574 A1 | 3/2006 | Priewe et al. | |
| 2006/0173237 A1 | 8/2006 | Jacquetin | |

FOREIGN PATENT DOCUMENTS

| | | |
|---|---|---|
| RU | 2187251 C1 | 8/2002 |
| RU | 2196518 C2 | 1/2003 |
| SU | 1475607 A1 | 4/1989 |
| WO | WO-0106951 A1 | 2/2001 |
| WO | WO-0152729 A2 | 7/2001 |
| WO | WO-0232346 A1 | 4/2002 |
| WO | WO-0239890 A2 | 5/2002 |
| WO | WO-02065921 A1 | 8/2002 |

OTHER PUBLICATIONS

Jacquetin. Utilisation du "TVT" dans la chirurgie . . . J. Gynecol. Obstet. Biol. Reprod. 29: 242-47 (2000).

deTayrac, et al. Prolapse repair by vaginal route using . . . Int. Urogynecol. J. (published online May 13, 2006).

* cited by examiner

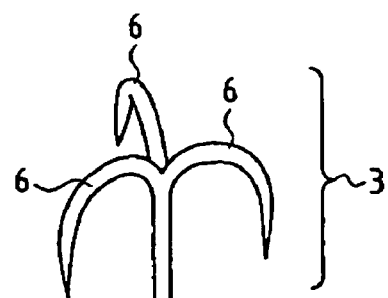
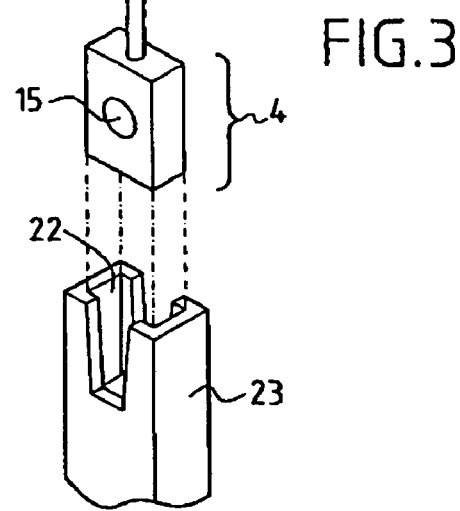
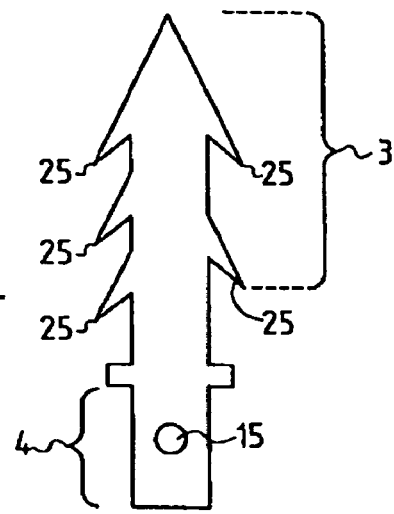
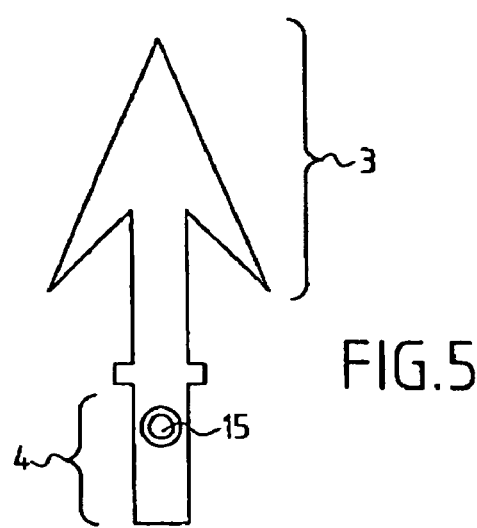
FIG.3
FIG.4
FIG.5

PARIETAL HOOK

This application claims benefit under 35 U.S.C. §119(e) of U.S. Provisional Patent Application No. 60/629,337 filed Nov. 22, 2004.

FIELD OF THE INVENTION

The technical domain of this invention is devices used for the treatment of problems with pelvic statics, for example such as stress incontinence, cystocele, rectocele and/or prolapse of the vaginal dome.

BACKGROUND OF THE INVENTION

In the above field, and particularly for the treatment of stress incontinence, it is known that a sub-urethral band with two opposite suspension arms can be inserted. Thus, patent U.S. Pat. No. 6,387,041 proposed fixing each of the arms of the band at a bone in the pubis, using a staple provided for this purpose force fitted into the said bone.

However, this technique is not always suitable, particularly due to the force that has to be applied to insert the staple into the bone.

Thus, another procedure has been proposed for placement of the sub-urethral band, consisting particularly of inserting suspension arms of this band into the ligaments and the transobturator muscles, possibly with a suture of the said arms onto the ligaments.

Such a procedure is particularly satisfactory for placement of the band with no tension.

However, during use it was found necessary to apply a slight tension to the band, particularly to its suspension arms, so as to better control the stress applied to the urethra, to form an obstacle to stress incontinence without preventing complete emptying of the bladder during voluntary micturition.

Immobilization of the suspension arms with suture stitches does not always enable a sufficiently fine adjustment of the tension applied to the band.

In order to provide a solution to this problem of optimum adjustment of the tension applied to the sub-urethral band and the position of the band, a problem that is also common to the treatment of other pathologies for example such as cystocele, rectocele or prolapse of the vaginal dome, the invention proposes a device for anchorage of a prosthetic implant with arms and flexible suspension links in muscle or ligament tissues.

BRIEF SUMMARY OF THE INVENTION

According to the invention, the anchorage device comprises:
  an elongated body,
  an anchor head located at one end of the body and provided with means of anchorage in the tissues,
  at least one orifice formed in the elongated body to attach a suspension arm that is associated with non-return means adapted to enable adjustment of the useful length of the arm and to prevent the arm from sliding in the direction opposite its direction of insertion.

The composition of the device according to the invention thus enables placement in two steps, for example for the treatment of stress incontinence using a sub-urethral band. Firstly, each device according to the invention with a suspension arm inserted into the attachment orifice is placed in the required region of ligaments. Once these placements have been made, a progressive tension is applied on the suspension arms, the presence of non-return means for each anchorage device according to the invention are such that tension can be relieved so as to test stress incontinence with simple and automatic blocking of the band without the need to make any sutures. Thus, the stress incontinence can be tested as much as necessary to vary the tension and optimize it to create an obstacle to stress incontinence, without preventing complete emptying of the bladder during micturition. Such an adjustment by successive iterations would not be as easy when using a procedure in which the arm is permanently immobilized by sutures.

According to the invention, non-return means can be made in any appropriate manner.

In one preferred but non-limitative embodiment of the invention, the attachment orifice passes through the body of the anchorage device, from an insertion face towards an exit face of the suspension arm and the non-return means comprise at least one tooth located at the exit face.

Thus, when tension is exerted on the suspension arm in the direction opposite its insertion direction, the arm engages on the tooth and the tooth blocks its movement automatically without any other action by the surgeon.

Preferably, the anchor orifice has a decreasing section from its insertion face to its exit face, to facilitate this self-attachment of the suspension arm.

According to the invention, the anchor head may be made in different ways, particularly depending on the tension that will be applied to the suspension arm to be fixed to it, or the configuration of the tissular area in which it will be integrated.

According to one characteristic of the invention, the anchor head has a lanceolate shape, for example such as a "V" arrow shape.

According to another characteristic of the invention, the anchor head has a series of anchor teeth distributed on each side of the body such that the anchor head has a fir tree shape.

According to yet another preferred but non-limitative embodiment of the invention, the anchor head comprises at least one anchor arm curved into a "U" shape, one segment of which is connected to the body while the other segment is approximately parallel to the body, the two segments being connected by an arch-shaped web that is concave towards the body of the device.

In order to anchor the device better into the tissues, the inner face of the "U" arm can then comprise at least one anchor tooth.

According to one embodiment of the invention, the anchor head comprises a single anchor arm curved in a "U" shape such that general shape of the anchorage device according to the invention is like a "U" or "J" shaped fishhook.

Such an embodiment of the device according to the invention as described above is particularly suitable for placement using a needle-holder. However, according to another characteristic of the invention, the body of the device may comprise means of adapting an insertion guide on the rod at the end opposite the anchor head, in order to facilitate placement of the anchorage device in the target tissues.

Such adaptor means can be made in any appropriate manner, for example by using a polygonal shaped section for the end opposite the anchor head of the body of the device, and therefore fitting into a housing complementary to the insertion guide.

These adaptor means can also be made in the form of roughnesses, enabling the anchorage device according to the invention to be controlled for example by a needle holder. Such roughnesses may then be made either at the end of the body of the anchorage device opposite the anchor head, or on the other hand at the middle of the elongated body, for example between the anchor head and the attachment orifice of a suspension arm.

According to the invention, the anchor head may have different shapes. Thus, the anchor head may have more than one anchorage arm curved in a "U" shape, and for example it may have three arms that may for example be arranged at 120° from each other such that the general shape of the anchorage device according to the invention is like a grappling hook.

According to the invention, the anchorage device could be made from any natural or manmade biocompatible material provided that it is sufficiently hard to perform its anchorage function in the tissues.

In one preferred embodiment, a slowly absorbed biocompatible material will be used and possibly chosen from among bio-absorbable polymers, for which the most frequently used in surgery are polyglycolides and polylactides. Obviously, the device according to the invention could also be made of metal.

Various other characteristics of the invention will become clear from the following description with reference to the attached drawings that illustrate different embodiments of an anchorage device according to the invention.

BRIEF DESCRIPTION OF THE DRAWINGS

FIG. 3 shows a perspective of a variant embodiment of an anchorage device according to the invention in the shape of a grappling hook.

FIG. 4 shows an elevation of a variant embodiment of an anchorage device according to the invention in the form a fir tree.

FIG. 5 shows an elevation of a variant embodiment of an anchorage device according to the invention in the form of an arrow.

DETAILED DESCRIPTION OF THE INVENTION

Figure 1:
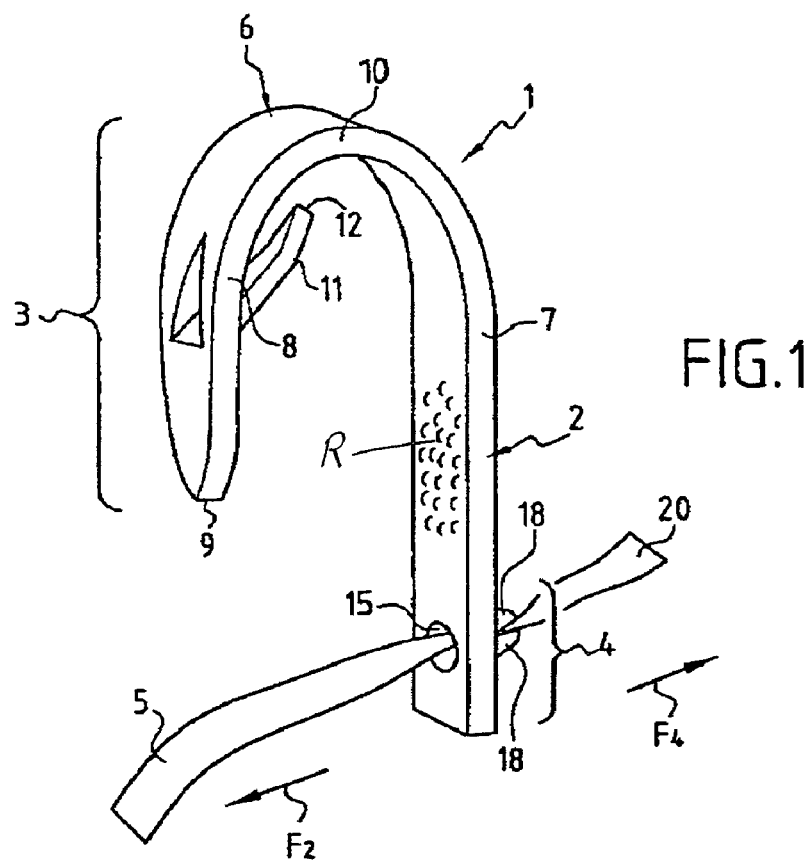
FIG. 1 shows a perspective of an embodiment of a fishhook shaped anchorage device according to the invention.
Figure 2:
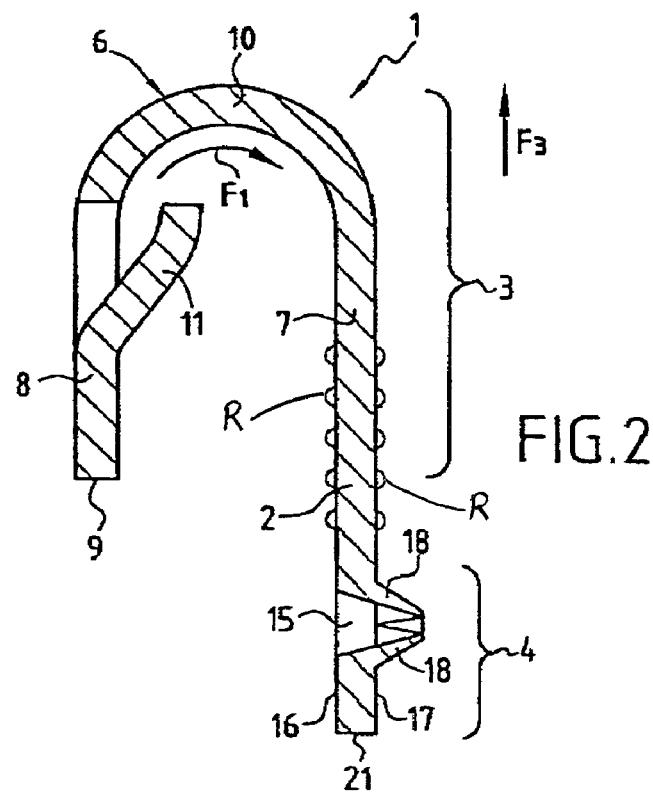
FIG. 2 shows a longitudinal section through the anchorage device according to FIG. 1.

An anchorage device according to the invention as illustrated in FIGS. 1 and 2 and designated as a whole as reference 1, comprises an elongated body 2 provided with an anchor head 3 at one end in the tissular regions such as regions of muscles or ligaments, and attachment means 4 for a suspension arm 5 of a sub-urethral band 5 at the end opposite the head 3.

In the example illustrated, the head 3 comprises a "U"-shaped arm 6 for which one segment 7 is connected to the body, while the other segment 8 is approximately parallel to the first segment 7 and the body 2. The second segment 8 then has a pointed end 9 and thus forms an anchorage means in the tissues. The first segment 7 is connected to the second segment 8 through an arch-shaped web 10, for which the concaveness is oriented towards the body of the device such that the general shape of the anchorage device according to this example embodiment is like a fishhook.

In the example illustrated, the anchor head 3 also comprises an anchor tooth 11 formed on the inner face of the U-shaped arm 6 that in the example illustrated is placed approximately in the connection region between the second segment 8 and the web 10, the tip 12 of the tooth 11 being oriented towards the connecting web 10 so as to prevent any rotation or accidental sliding of the device 1 in the tissues to which it is attached along the direction of the arrow $F_1$.

On the side opposite the head 3, the body 2 is provided with non-return attachment means 4 of the suspension arm 5. According to the example illustrated, these non-return attachment means comprise an orifice 15 passing through the elongated body 2 from a so-called insertion face 16 as far as a so-called exit face 17 of the body 2. According to the example illustrated, the insertion face 16 faces the second segment 8 and the exit face 17 is oriented outwards but an inverse arrangement could equally well be envisaged.

According to the example illustrated, the cross-section of the attachment orifice 15 decreases from the insertion face 16 towards the exit face 17.

The orifice 15 is also used with non-return means, in the example illustrated comprising two teeth 18 facing each other at the exit face for an attachment or automatic stop of the suspension arm 5 when tension is applied along the direction of arrow $F_2$ opposite to the insertion direction. Note that this non-return effect is improved by choosing the diameter of the orifice 15 so that it is smaller than the width of the suspension arm 5.

According to the example illustrated, the anchorage device 1 also comprises two series of roughnesses 16 formed on its two faces at the body 2 between the anchor head 3 and the attachment means 4 of the suspension arm, so as to enable the anchorage device to accept load for example through a needle-holder.

Such an anchorage device 1 according to the invention is used as follows.

Firstly, the end of a suspension arm 5 is engaged in the orifice 15 projecting from the exit face 17 so that the arm length 20 is long enough to be gripped with two fingers or using a clip.

The device 1 is then engaged in the tissues so as to orient the convexity of the anchor head 3 in the insertion direction $F_3$ to have lower resistance to penetration into the tissues.

When the optimum position of the device 1 is reached, the surgeon stops the thrust applied on the device at its body and then applies a tension in the direction of the arrow $F_4$ onto the part 20 of the suspension arm 5 to adjust the useful length of the arm and the tension in the band fixed to the said arm. In this case, the useful length is the length of the part of the arm that effectively contributes to the suspension and resists forces, as opposed to the arm part 20 that could be qualified as a free part.

Note that tension in the reverse direction F.sub.2 automatically attaches the suspension arm onto the two teeth 18 which therefore perform a non-return function, such that the suspension arm 5 acts through the device 1 and is literally anchored into the tissues at the location at which the device 1 is inserted. Thus, by use of this anchorage device 1, the surgeon can very quickly position the suspension arms in the preferred anchorage area and then adjust the useful length and the tension applied on the suspension arms. This adjustment should be made in small steps, so as to not exceed the maximum tension beyond which micturition or total emptying of the bladder is no longer possible. However, provided that the tension and position of the arm are adjustable by applying a simple tension, it is possible to proceed by trial and error and thus achieve the optimum tension after carrying out a series of tests. Once the tension has been adjusted, the surgeon will cut off the excess portion of the part 20 of the suspension arm, taking care not to cut the anchorage device too short so as to maintain the reliable anchorage of the suspension arm on the anchorage device.

Note also that the anchorage device according to the invention may be used either for traditional surgery, or for laparoscopic surgery using a specific ancillary or a needle-holder.

According to the invention, the head 3 of the anchorage device 1 may have more than one curved arm 6 as illustrated in FIGS. 1 and 2. Thus, FIG. 3 illustrates another embodiment of an anchor head 3 with three U arms 6, such that the anchorage device 1 is in the shape of a grappling hook.

Note that according to the example illustrated, the body 2 of the anchorage device 1 is provided with an approximately rectangular prismatic cross-section at the end opposite the anchor head, such that the end 21 of the body 2 can be engaged in a recess 22 with a complementary shape formed in an ancillary, for example such as a rigid or semi-rigid insertion guide 23, only one end of which is illustrated in FIG. 3. Thus, the shape of the end 21 of the body 2 forms adaptor means of the device 1 onto the guide 23. Obviously, any other embodiment of means of adapting the device onto an ancillary could be considered within the framework of the invention.

According to the invention, the anchor head may be made in various manners other than those illustrated in FIGS. 1 and 3.

Thus, FIG. 4 illustrates another embodiment on which the anchor head 3 is provided with a series of teeth 25 distributed on each side of the body 2, thus assuring that the device 1 is in the shape of a fir tree.

Similarly, FIG. 5 illustrates another embodiment by which the anchor head 3 is in the form of a "V" arrow.

Obviously, other modifications could be made to the invention without going outside its scope.

The invention claimed is:

1. A soft tissue surgical anchoring device comprising:
   an elongated body;
   an anchor head configured to anchor soft tissue and coupled with the elongated body by a generally U-shaped portion such that a terminal portion of the anchor head is generally parallel with the elongated body and a tooth depends from the terminal portion towards a concave portion of the U-shaped portion;
   an orifice disposed through the elongated body and having an entrance and an exit, wherein the entrance is disposed on a first face of the elongated body member and the exit is disposed on a second face of the elongated body member, with second face on a portion that is opposite from the concave portion of the U shaped portion such that a path defined from the entrance to the exit moves in a direction away from the terminal portion; and
   a pair of teeth forming a non-return mechanism, the teeth disposed on the second face of the elongated body and are directed away from the exit so as to form a narrowing pathway relative to the entrance and configured so that movement of a flexible member is permitted in a direction of the path and hindered in a direction opposite the path.

2. The anchoring device according to claim 1, wherein the terminal portion has a lanceolate shape.

3. The anchoring device according to claim 1, wherein the anchoring device is made of a slowly absorbed biocompatible material.

* * * * *